United States Patent
Nelson et al.

(10) Patent No.: US 11,136,281 B2
(45) Date of Patent: Oct. 5, 2021

(54) PROCESS OF SEPARATING UNSATURATED HYDROCARBONS FROM SATURATED HYDROCARBONS WITH LOW ENERGY CONSUMPTION

(71) Applicant: Sulzer Management AG, Winterthur (CH)

(72) Inventors: Cole Nelson, Cypress, TX (US); Venkata K. Ramanujam, Sugar Land, TX (US)

(73) Assignee: SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 16/847,644

(22) Filed: Apr. 13, 2020

(65) Prior Publication Data

US 2020/0239388 A1 Jul. 30, 2020

Related U.S. Application Data

(63) Continuation-in-part of application No. 14/640,583, filed on Mar. 6, 2015, now abandoned.

(Continued)

(51) Int. Cl.
*C07C 7/04* (2006.01)
*C07C 7/00* (2006.01)
(Continued)

(52) U.S. Cl.
CPC ................ *C07C 7/04* (2013.01); *B01D 3/146* (2013.01); *B01D 5/006* (2013.01); *B01D 5/0075* (2013.01);
(Continued)

(58) Field of Classification Search
CPC .. C07C 7/005; C07C 7/04; C10G 7/00; B01D 3/143
See application file for complete search history.

(56) References Cited

U.S. PATENT DOCUMENTS 2,427,954 A 9/1947 Frey
2,438,456 A 3/1948 Russell et al.
(Continued)

OTHER PUBLICATIONS

De Haan, 2013, Industrial Separation Processes—Fundamentals. De Gruyter (Year: 2013).*
(Continued)

*Primary Examiner* — Youngsul Jeong
(74) *Attorney, Agent, or Firm* — Global IP Counselors, LLP

(57) ABSTRACT

Apparatuses, systems and methods for separating highly pure unsaturated olefinic hydrocarbon stream with zero cooling water and or steam consumption, with minimum possible capital investment and uncompromised operational ease are disclosed herein from a mixture of hydrocarbon stream consisting of saturated and unsaturated hydrocarbons. Embodiments of the invention are directed to producing a hydrocarbon stream containing polymer, chemical grade ethylene, propylene, butylenes, isoprene, hexane stream which are of value in manufacturing chemicals, polymers, and rubbers. Embodiments of the process provided can be applied to concentrating ethylene, propylene, butylenes, cyclopentadiene, isoprene, 2 methyl butene-2, isopentane, hexene etc.

9 Claims, 4 Drawing Sheets

Related U.S. Application Data

(60) Provisional application No. 61/949,063, filed on Mar. 6, 2014.

(51) Int. Cl.
*C07C 5/03* (2006.01)
*B01D 5/00* (2006.01)
*B01D 3/14* (2006.01)

(52) U.S. Cl.
CPC .............. *B01D 5/0087* (2013.01); *C07C 5/03* (2013.01); *C07C 7/005* (2013.01)

(56) References Cited

U.S. PATENT DOCUMENTS

| | | | |
|---|---|---|---|
| 3,260,057 A | 7/1966 | Becker | |
| 3,821,323 A * | 6/1974 | Schulze et al. | B01J 23/60 585/261 |
| 5,435,436 A * | 7/1995 | Manley | B01D 5/0045 202/172 |
| 6,413,378 B1 | 7/2002 | Kanauchi et al. | |
| 7,842,847 B2 | 11/2010 | Panditrao et al. | |
| 8,182,654 B2 | 5/2012 | Sechrist et al. | |
| 2011/0130604 A1 * | 6/2011 | Gartside | C07C 5/2506 585/324 |

OTHER PUBLICATIONS

National Institute of Standards and Technology, NIST Chemistry WebBook (Year: 2017).*
De Haan, Andre Bosch; Industrial Separation Processes—Fundamentals; 2013; 2 pages.
National Institute of Standards and Technology; May 22, 2017; 4 pages.
Jehle, W. et al.; "Separtion of glycol and water from coolant liquids by evaporation, reverse osmosis and pervaporation"; Journal of Membrane Science; vol. 102; 1995; pp. 9-19.

* cited by examiner

PROCESS OF SEPARATING UNSATURATED HYDROCARBONS FROM SATURATED HYDROCARBONS WITH LOW ENERGY CONSUMPTION

CROSS-REFERENCE TO RELATED APPLICATIONS

This application is a continuation-in-part of, and incorporates by reference the entire disclosure of, U.S. patent application Ser. No. 14/640,583, filed Mar. 6, 2015. This application claims priority from, and incorporates by reference the entire disclosure of, U.S. Provisional Patent Application No. 61/949,063 filed on Mar. 6, 2014.

BACKGROUND OF THE INVENTION

A mixture of unsaturated hydrocarbons and saturated hydrocarbons are produced in the process of catalytic cracking, steam cracking, thermal cracking or dehydrogenation, hydrogenation process. Unsaturated hydrocarbons present in the mixture are building blocks for producing numerous chemicals, polymers, resins and rubbers. Hence it is highly desirable to have ultra pure unsaturated hydrocarbon stream. Various separation processes, such as traditional fractional distillation, pressure swing adsorption, or a combination of adsorption and distillation, extraction, extractive distillation, sponging distillation or combination of any of the above, are used to separate the unsaturated and saturated hydrocarbons.

The relative volatility difference between the unsaturated hydrocarbon and its saturated counterpart is so low that the separation process invariably consumes excessive energy with an excessive number of distillation trays. A number of alternative schemes such as high-pressure distillation, low-pressure distillation with heat pump, and divided wall column are suggested in the prior art to achieve the desired unsaturated hydrocarbon stream with minimum possible energy consumption.

FIELD OF THE INVENTION

The claimed invention and the apparatuses and methods are intended to obtain unsaturated and saturated hydrocarbon streams in particular light olefins containing 2-6 carbons with minimum possible energy and investment and ease and reliable operation, one of which is otherwise sacrificed. Such apparatuses and methods would allow more efficient operation and system design and operating conditions.

Typically the unsaturated hydrocarbons and saturated hydrocarbons, particularly hydrocarbons containing 2 to 6 carbon atoms are separated using tall distillation columns, typically separated physically into two distillation columns. Alternately, a heat pump system is used wherein the overheads of the distillation column are compressed to high enough pressure to provide the required heat to the reboiler.

The present invention provides an improvement to the traditional distillation and heat pump system and other combinations by employing intermediate compressor and integrating the condenser and reboiler and exploiting the natural behavior of the unsaturated hydrocarbons and saturated hydrocarbons with respect to pressure to minimize the energy and capital and simultaneously keeping the operations simple and stable.

The present invention can be applied to systems consisting of unsaturated hydrocarbons and saturated hydrocarbons or isomers of saturated or unsaturated hydrocarbons or unsaturated hydrocarbons, boiling point difference between the components of which are less that 10° C., preferably less than 5° C. and separation of which require tall columns or extraction solvent or combination thereof.

SUMMARY OF THE INVENTION

In various embodiments, system of apparatuses and operating conditions for separating the unsaturated hydrocarbons from saturated hydrocarbons, particularly hydrocarbons containing 2 to 6 carbon atoms are disclosed. The apparatuses comprise of a distillation column, a compressor, heat exchangers for reboiler, condenser systems, and coolant systems, reflux drum and pumps for pumping the saturated hydrocarbon and unsaturated hydrocarbon.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION OF EXEMPLARY EMBODIMENTS

Figure 1:
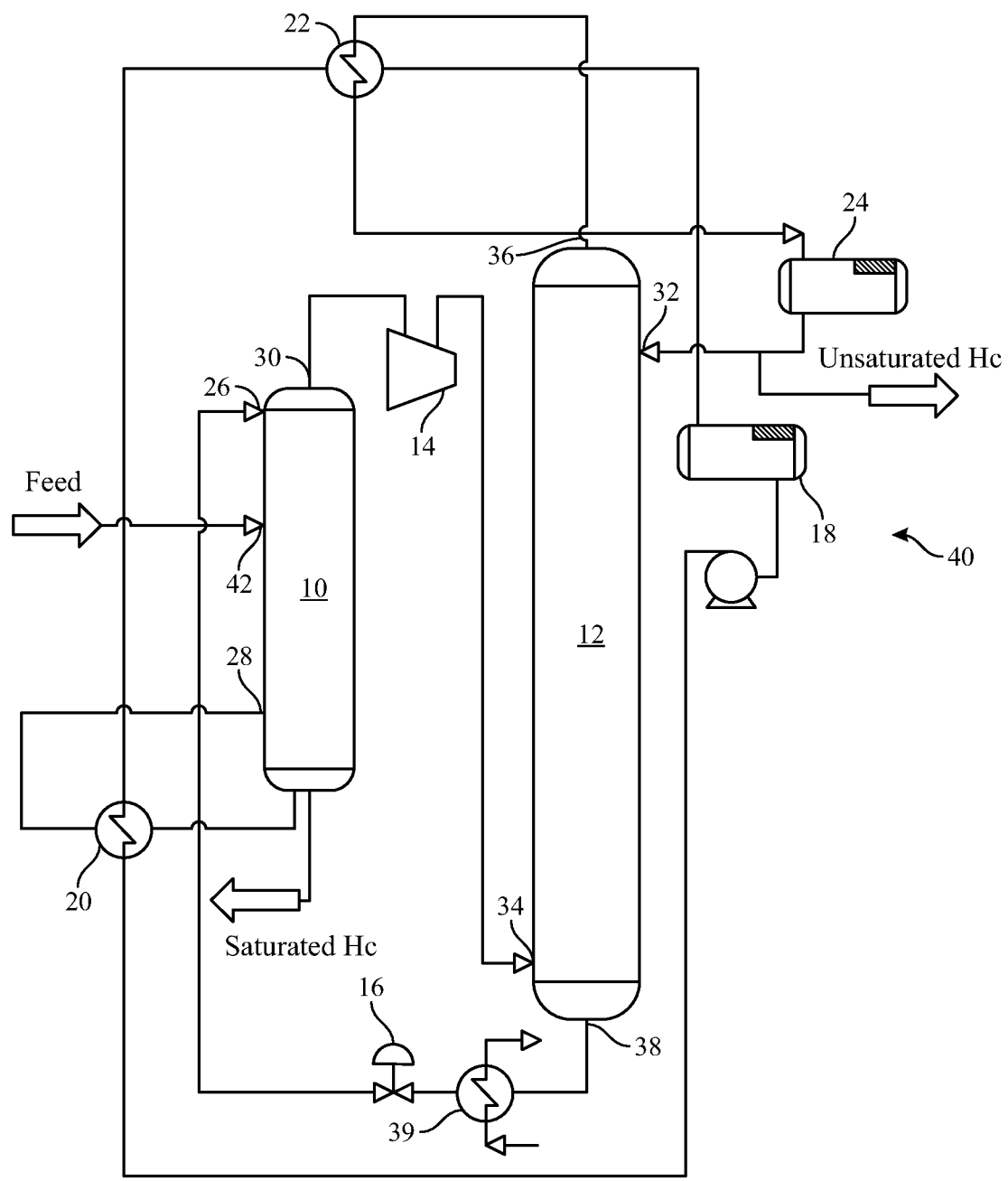
FIG. 1 shows an illustrative unsaturated and saturated hydrocarbon separation system with a low-pressure stripper column feed point.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the ability of persons of ordinary skill in the relevant art.

Referring to the drawings in general, it will be understood that the illustrations are for the purpose of describing a particular embodiment of the disclosure and are not intended to be limiting thereto. Drawings are not necessarily to scale.

While most of the terms used herein will be recognizable to those of skill in the art, it should be understood, however, that when not explicitly defined, terms should be interpreted as adopting a meaning presently accepted by those of skill in the art.

"Unsaturated hydrocarbon," as used herein, refers to, for example, light olefins such as ethylene, propylene, butylenes, methyl butenes and its isomers, cis and, or trans pentene, hexanes and similar hydrocarbons. "Saturated Hydrocarbons" and as used herein, refers to Ethane, Propane, Butane, Pentane, Methyl Butane, Hexane and similar hydrocarbons.

In the catalytic cracking process or In the thermal cracking, in the presence of steam of liquid fractions of petroleum, such as LPG, Naphtha, Diesel and heavies for production of ethylene and or propylene, or in the propane or Butane dehydrogenation process, a hydrocarbon liquid fraction consisting of unsaturated hydrocarbons and saturated hydrocarbons is produced. Also pyrolysis gasoline, a steam cracker hydrocarbon product consists of hydrocarbon components ranging from 4 carbon atoms to more than 10 carbon atoms. Among these, of importance to the field of innovation are mono olefins and diolefins such as ethylene, propylene, butylenes, cyclopentadiene (CPD), methyl cyclopentadiene, cis and/or trans 1,3 pentadienes (Pips), Isoprene, 2-methyl-butene-1, 2-methyl-butene-2, pentene, hexane and similar hydrocarbon molecules containing up to 6 carbons. These compounds are used in wide variety of industries to make chemicals, polymers, rubbers etc.

In various embodiments, apparatuses for obtaining streams consisting of single component or components necessary for making specific chemicals and polymers are disclosed. The apparatuses comprise: distillation columns, a compressor, heat exchangers for reboiler and condenser, heat exchanger for cooling bottoms product from the high-pressure distillation column, pumps for pumping product, reflux and water, vessels for keeping the overhead liquid and circulating cooling water.

Figure 2:
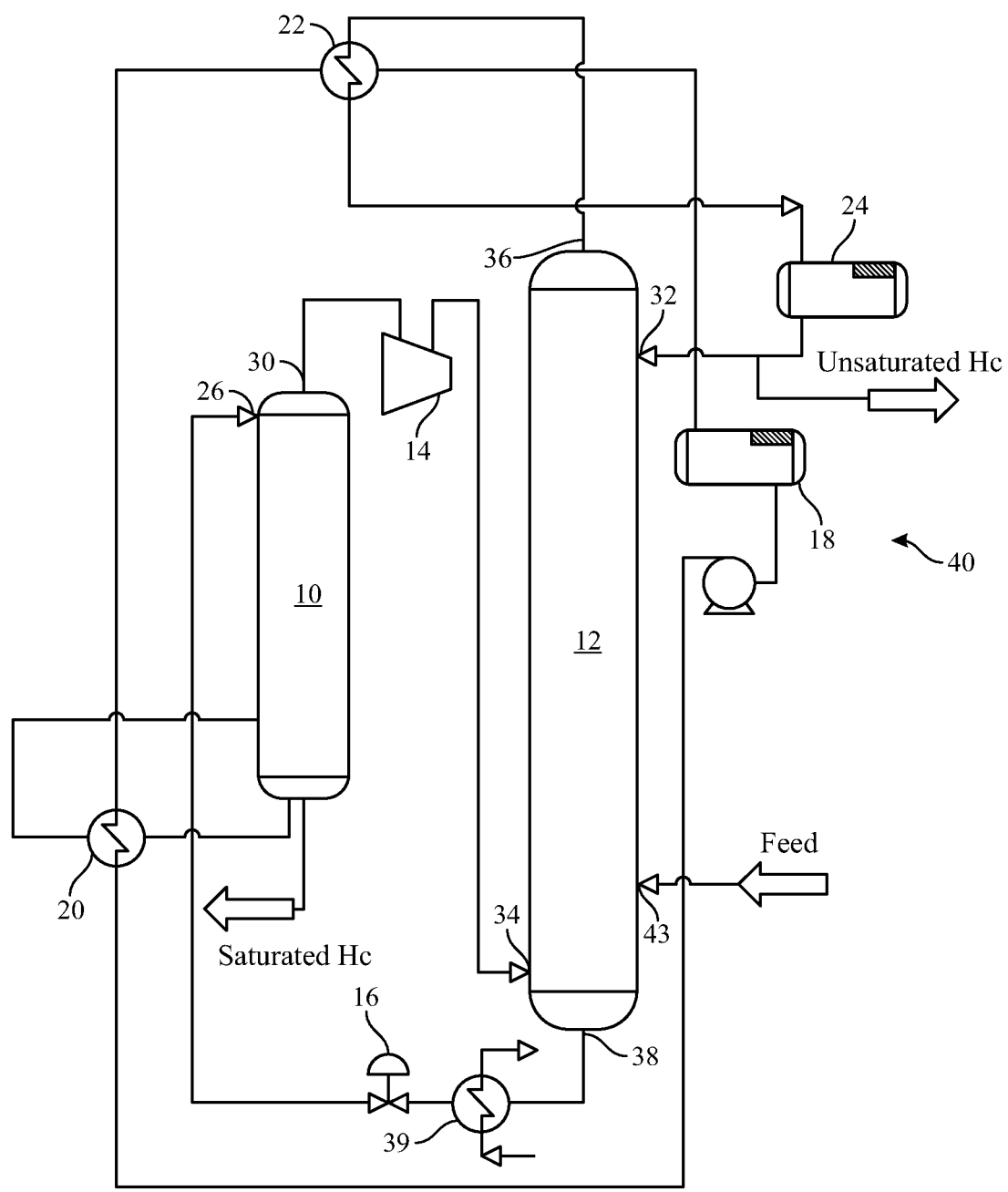
FIG. 2 shows an illustrative unsaturated and saturated hydrocarbon separation system with a high-pressure rectification column feed point.

Embodiments of the invention are directed to processes for the production of a purified unsaturated hydrocarbon stream such as ethylene, propylene, butylenes, 2 methyl butene-1, 2 methyl butene-2, Isoprene, cis and trans pentene, Hexene or similar using a system that employs a specific arrangement of distillation column and compressor and operating conditions to reduce the energy consumption, capital investment while at the same time achieving a stable operation. FIGS. 1 and 2 show an illustrative unsaturated and saturated hydrocarbon separation system 40. System 40 couples together a low-pressure distillation column 10 and a high-pressure distillation column 12 using a direct coupled compressor 14. Compressor 14 is operated to have a pressure ratio of 1.5 to 4, depending on a carbon number in the feed provided to system 40. The feed can be introduced either in the low-pressure section of low-pressure distillation column 10 at a feed inlet 42 (FIG. 1) or in the high-pressure section of the high-pressure distillation column 12 at a feed inlet 43 (FIG. 2).

System 40 employs low-pressure distillation column 10 as a stripping column and high-pressure distillation column 12 as a rectification column. Low-pressure distillation column 10 includes a first low-pressure inlet 26, a second low-pressure inlet 28, a feed inlet 42 (e.g., see FIG. 1) and a low-pressure overheads outlet 30. High-pressure distillation column 12 includes a high-pressure inlet 32, a high-pressure bottoms inlet 34, a high-pressure overheads outlet 36, a high-pressure bottoms outlet 38, and feed inlet 43 (e.g., see FIG. 2). Compressor 14 compresses the overhead from low-pressure distillation column 10, which is introduced to the bottom of high-pressure distillation column 12 as a stripping medium. High-pressure liquid from the bottom of high-pressure distillation column 12 is de-pressurized to low-pressure column conditions through a valve 16 (e.g., a Joules Thomson valve or equivalent) and is introduced to the top of low-pressure distillation column 10.

System 40 includes a vessel 18, a reboiler/condenser 20, and a condenser/reboiler 22 that form a closed-loop cooling system. Cooling water with or without anti-freeze, depending on the application, is stored in vessel 18 and is pumped and circulated through reboiler/condenser 20 and a condenser/reboiler 22 in a sequential manner such that one provides the heat duty required for the other. The overhead vapor from high-pressure distillation column 12 is condensed, and stored in a vessel 24. A portion of the condensed vapor is refluxed to high-pressure distillation column 12 and the remainder is pumped as a pure unsaturated product stream. The liquid bottoms product from the bottom of low-pressure distillation column 10 is pumped as a product stream and contains predominantly the saturated hydrocarbon.

System 40 includes a heat exchanger 39 that cools the high-pressure bottoms from high-pressure distillation column 12. Heat exchanger 39 uses an external coolant source (e.g., from a refrigeration station etc.) to remove the external enthalpy added to the overall system because of the work done by the compressor. Inclusion of heat exchanger 39 enables the coolant loop (e.g., vessel 18, reboiler/condenser 20, and condenser/reboiler 22) to operate in a self-sustaining manner.

In various embodiments of the apparatuses, the distillation columns are vessels with trays or packing as internals and may contain partition plates or heads to separate the high-pressure and low-pressure zone or may implement two columns physically separated from each other and or mounted on top of each other.

In various embodiments the apparatuses, distillation columns 10, 12 are operated at pressure ratios between 1.5 and 4.0 to keep the system in heat balance and to provide reasonable temperature gradient for heat transfer between the low-pressure distillation column reboiler 20 and the high-pressure distillation column condenser 22, which differs from traditional distillation columns where both the stripping and rectification occurs at same pressure.

In various embodiments, the arrangement shown in FIG. 1 and FIG. 2 is operated such that the liquid recycle from the high-pressure distillation column 12 to low-pressure distillation column 10 acts as an operating variable for varying feed compositions.

Figure 3:
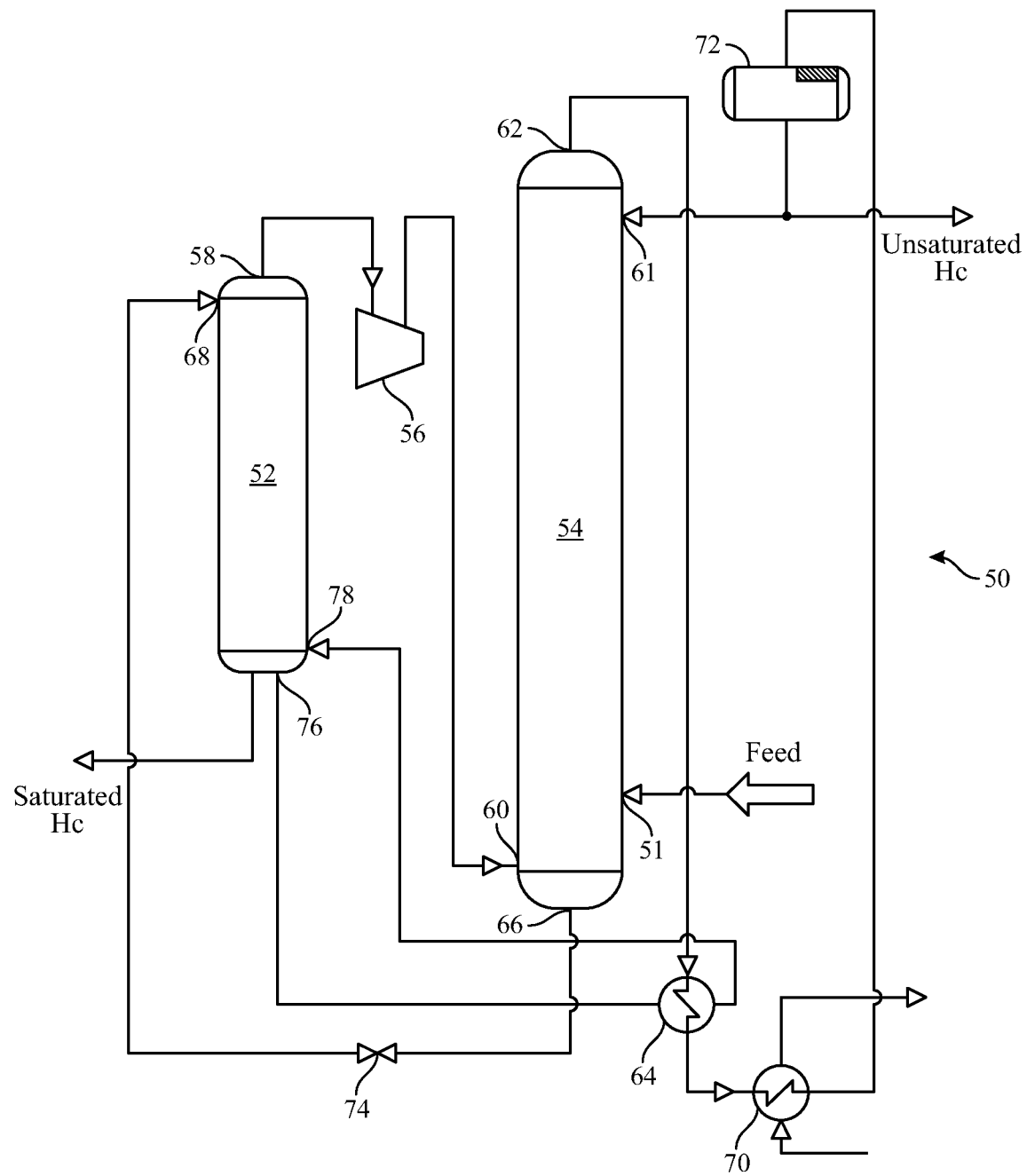
FIG. 3 shows an illustrative unsaturated and saturated hydrocarbon separation system with a high-pressure rectification column feed point.
Figure 4:
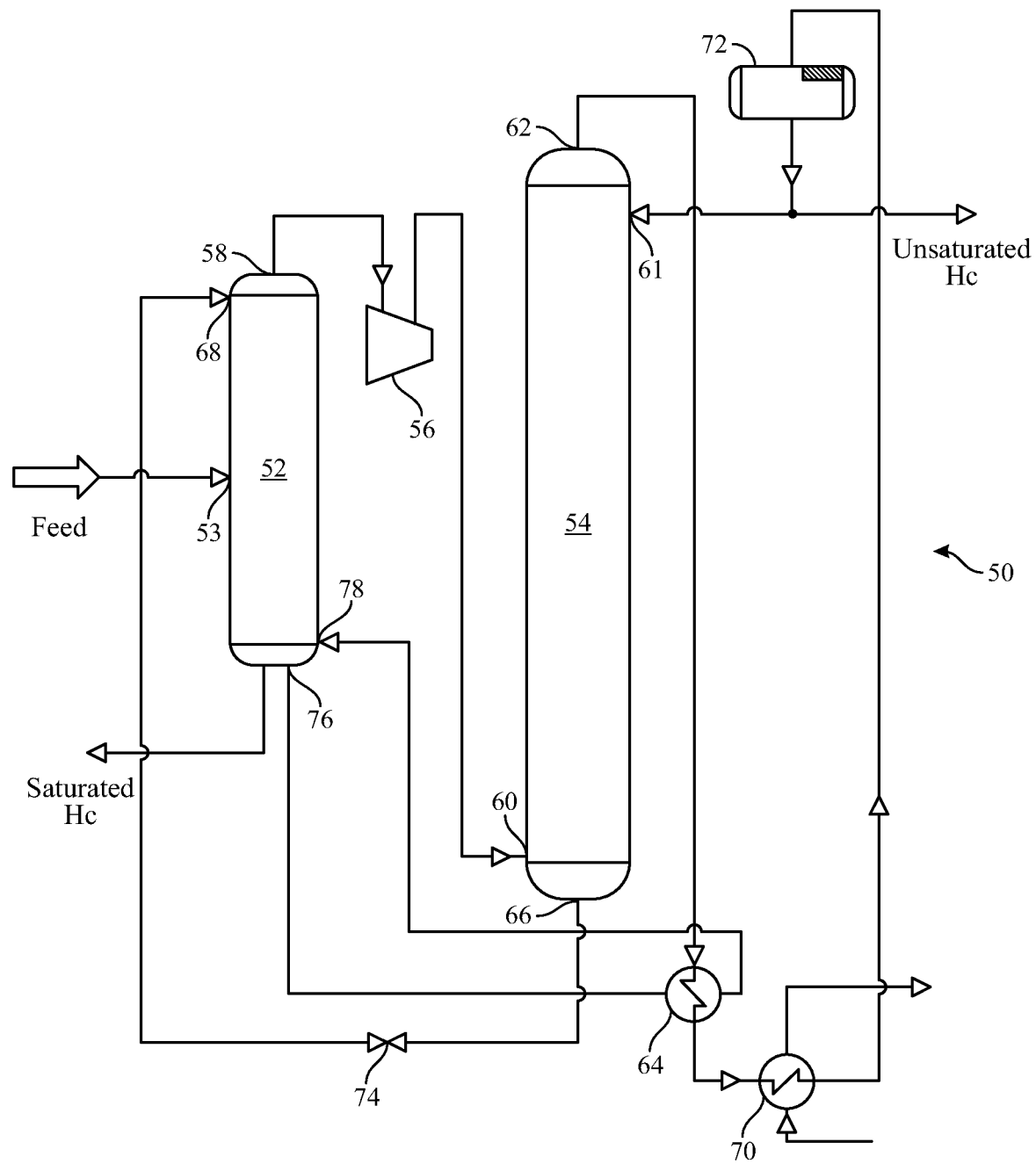
FIG. 4. shows an illustrative unsaturated and saturated hydrocarbon separation system with a low-pressure stripping column feed point.

FIGS. 3 and 4 illustrate embodiments of an unsaturated and saturated hydrocarbon separation system 50 with a high-pressure rectification column feed point (FIG. 3) a low-pressure stripping column feed point (FIG. 4). System 50 includes a low-pressure distillation column 52 that is used as a stripping column and a high-pressure distillation column 54 that is sued as a rectification column. Low-pressure distillation column 52 includes a low-pressure inlet 68, a feed inlet 53 (e.g., see FIG. 4), a low-pressure overheads outlet 58, a bottoms outlet 76, and a bottoms inlet 78. High-pressure distillation column 54 includes a high-pressure inlet 61, a high-pressure bottoms inlet 60, a high-pressure overheads outlet 62, a high-pressure bottoms outlet 66, and feed inlet 51 (e.g., see FIG. 3). A compressor 56 is fluidly coupled between low-pressure distillation column 52 and high-pressure distillation column 54 and compresses lights from a low-pressure overheads outlet 58 of between low-pressure stripping column 52. The compressed fluids from compressor 56 are fed to a high-pressure bottoms inlet 60 of high-pressure distillation column 54.

In some embodiments, a feed enters system 50 via feed inlet 51 of high-pressure distillation column 54 (FIG. 3). In other embodiments, the feed enters system 50 via feed inlet 53 of low-pressure distillation column 52 (FIG. 4). High-pressure overheads leave high-pressure distillation column 54 via high-pressure overheads outlet 62. The high-pressure overheads pass to a heat exchanger 64 where heat is exchanged between the high-pressure overheads and a bottoms product of low-pressure distillation column 52. Heat exchanger 64 performs the dual role of reboiler (for low pressure column) and condenser (for the high pressure column). The pinch across this exchanger is directly correlated to the pressure ratio across the compressor.

After exiting heat exchanger 64, the high-pressure overheads pass through a heat exchanger 70 to be further cooled by exchanging heat with coolant that circulates therethrough. For example, heat exchanger 70 contributes small vapor condensation and major subcooling. Temperature of the fluids leaving heat exchanger 64 may be around 36° C. and the temperature leaving heat exchanger 70 may be around 33° C. The coolant may be a feed stream from another process that is at a lower temperature than the high-pressure overheads or may be part of a refrigeration system etc. The cooled high-pressure overheads then pass to an overhead accumulator 72. A portion of the fluids in overhead accumulator 72 are returned to high-pressure distillation column 54 via high-pressure inlet 61 as reflux and the remainder are produced as an unsaturated hydrocarbon feed.

A high-pressure bottoms product exits high-pressure distillation column 54 via high-pressure bottoms outlet 66 and is fed to low-pressure inlet 68 of low-pressure stripping column 52. In some aspects, a valve 74 may be used to reduce the pressure of the high-pressure bottoms product to match the pressure at low-pressure inlet 68. A saturated hydrocarbon feed exits as a bottoms product from low-pressure stripping column 52. Low-pressure stripping column 52 also includes low-pressure bottoms outlet 76 that directs the low-pressure bottoms product from low-pressure stripping column 52 to heat exchanger 64 and low-pressure bottoms inlet 78 that receives the low-pressure bottoms product after the low-pressure bottoms product has exchanged heat with the high-pressure overheads from high-pressure distillation column 54.

In various embodiments, the arrangements shown in FIGS. 1-4 can be used in combination with a selective hydrogenation unit to saturate the alkynes containing 2-6 carbons.

Table 1 below details various parameters of systems of the instant disclosure. As shown in Table 2 below, the systems of the disclosure provide a process that consumes less energy than traditional prior art systems.

TABLE 1

| Description -Title | Units | Scheme 1 Traditional Splitter | Scheme 2 Heat Pump System | Scheme 3 Heat integrated Distillation System (FIGS. 3 and 4) |
|---|---|---|---|---|
| Main Column | | | | |
| Top Pressure | kg/cm$^2$g | 14.8 | 3.54 | 14.5 |
| Bottom Pressure | kg/cm$^2$g | 16.5 | 5.3 | 15.7 |
| No. Of Stages | | 147 | 143 | 126 |
| Top Temp | ° C. | 37 | −3.2 | 36 |
| Bottom Temp | ° C. | 51 | 9.5 | 44 |
| Secondary Column | | | | |
| Top Pressure | kg/cm$^2$g | NA | NA | 5 |
| Bottom Pressure | kg/cm$^2$g | NA | NA | 5.25 |
| No. Of Stages | | NA | NA | |
| Top Temp | ° C. | NA | NA | 4.2 |
| Bottom Temp | ° C. | NA | NA | 9.3 |
| Main Column reboiler Duty | MMKCAL/h | 10.37 | 7.7 | 0 |
| Utilty Consumption (LP Steam) | kg/h | 20740 | 0 | 0 |
| Main Column Condenser Duty | MMKCAL/h | −10.38 | −8.3 | −13.26 |
| Utilty Consumption (CW) | m$^3$/h | 1297.5 | 0 | 0.0 |
| Compressor - Compression Ratio | | NA | 4.54 | 2.8 |
| Polytropic work (Electricity) | KW | NA | 2140 | 1913 |
| Condensing Exchangers | MMKCAL/h | 10.4 | 2.1 | 1.85 |
| Utility Cooling Water | m$^3$/h | 1040 | 210 | 185 |
| Feed Flowrate | ton/h | 14.5 | 14.5 | 14.5 |
| Feed Composition | C3=/C3 | 70/27 | 70/27 | 70/27 |
| Propylene Purity | % | 99.5 | 99.5 | 99.5 |
| Propylene Recovery | % | 98.3 | 98.3 | 98.4 |

Some of the advantages of the foregoing inventive system include:

1. Zero continuous external steam Consumption
2. Exploits the natural pressure behavior of components in stripping and rectification section
3. Stripping and rectification sections of the distillation column are operated at their best efficiency point compared to traditional distillation
4. Lower electricity consumption compared to a mechanical vapor recompression (MVR) system
5. Stable and ease to operate compared to MVR system
6. Less complexity compared to heat integrated distillation column.

From the foregoing description, one skilled in the art can easily ascertain the essential characteristics of this disclosure, and without departing from the spirit and scope thereof, can make various changes and modifications to adapt the disclosure to various usages and conditions. The embodiments described herein above are meant to be illustrative only and should not be taken as limiting of the scope of the disclosure, which is defined in the following claims.

What is claimed is:

1. A method for producing an unsaturated hydrocarbon stream, the method comprising:

providing a feed comprising saturated and unsaturated hydrocarbons to a hydrocarbon separation system, the hydrocarbon separation system comprising:
a low-pressure distillation column;
a high-pressure distillation column;
a compressor comprising a compressor inlet coupled to the low-pressure distillation column and a compressor outlet coupled to the high-pressure distillation column;
a feed inlet for receiving the feed coupled to one of the low-pressure distillation column and the high-pressure distillation column for receiving the feed; and
a closed-loop recirculating coolant system comprising:
   a condenser coupled to the high-pressure distillation column; and
   a reboiler coupled to the low-pressure distillation column with the coolant being circulated through the condenser coupled to the high-pressure distillation column;
compressing, via the compressor, an overhead product from the low-pressure distillation column;
feeding the compressed overhead product to the high-pressure distillation column;
feeding a bottoms product from the high-pressure distillation column to a heat exchanger to exchange heat between the bottoms product of the high-pressure distillation column and a coolant from an external coolant source passing through the heat exchanger;
feeding the heat-exchanged bottoms product from the heat exchanger to the low-pressure distillation column; and
producing an unsaturated hydrocarbon stream from the high-pressure distillation column;
wherein the high-pressure distillation column operates at a pressure range of 12 to 20 kg/cm$^2$ g and the low-pressure distillation column operates at a pressure range of 3 to 8 kg/cm$^2$ g.

2. The method of claim 1, wherein the feed inlet is coupled to the low-pressure distillation column.

3. The method of claim 1, wherein the feed inlet is coupled to the high-pressure distillation column.

4. The method of claim 1, wherein the low-pressure and high-pressure distillation columns are operated at a pressure ratio of between 2-4, wherein the pressure ratio refers to the pressure of the high-pressure distillation column to the pressure of the low-pressure distillation column.

5. The method of claim 1, wherein the high-pressure distillation column operates at a temperature range of 30 to 100° C.

6. The method of claim 1, wherein the low-pressure distillation column operates at a temperature range of 4 to 45° C.

7. The method of claim 1, wherein the hydrocarbon separation system is used in combination with a selective hydrogenation unit to saturate alkynes.

8. The method of claim 1, further comprising:
removing, from the low-pressure distillation column, a bottoms product comprising saturated hydrocarbons; and
wherein the bottoms product removed from the low-pressure distillation column is at a pressure of between 3-8 kg/cm$^2$ g.

9. The method of claim 1, further comprising:
removing, from the low-pressure distillation column, a bottoms product comprising saturated hydrocarbons; and
wherein the bottoms product removed from the low-pressure distillation column is at a temperature of 5-20° C.

* * * * *